United States Patent [19]

Maizenberg

[11] Patent Number: 4,575,338

[45] Date of Patent: Mar. 11, 1986

[54] BALL TYPE BUR GRIPPING MECHANISM FOR DENTAL HANDPIECE

[75] Inventor: Leonid I. Maizenberg, Chicago, Ill.

[73] Assignee: Sybron Corporation, Rochester, N.Y.

[21] Appl. No.: 673,822

[22] Filed: Nov. 21, 1984

[51] Int. Cl.[4] ............................................. A61C 1/08
[52] U.S. Cl. .................................... 433/126; 279/1 C
[58] Field of Search ....................... 433/126, 128, 129;
   279/1 C, 75, 72, 71, 74, 30, 1 B, 23, 1 F, 38, 50, 82

[56] References Cited

U.S. PATENT DOCUMENTS 4,209,182  6/1980  Sheldon ............................. 279/1 B
4,493,645  1/1985  Nakanishi ......................... 433/127

Primary Examiner—Robert Peshock
Attorney, Agent, or Firm—Robert A. Gerlach; Robert J. Bird

[57] ABSTRACT

A dental handpiece head having a bur-gripping mechanism which includes a spring-loaded ball carrier urged by the spring into operative engagement with a tapered ramp which in turn forces the several balls into clamping engagement with the shank of a dental bur positioned in the central bore of the ball carrier. The balls bite into the shank providing positive engagement. Downward force applied to the ball carrier against the spring, by a cam lever or by a pushbutton, releases the engagement.

9 Claims, 7 Drawing Figures

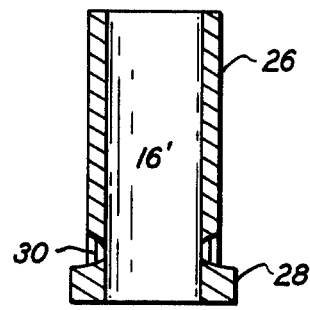
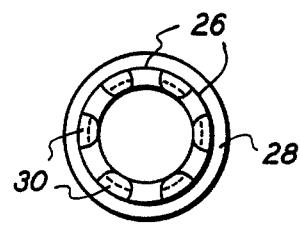
FIG. 2          FIG. 3
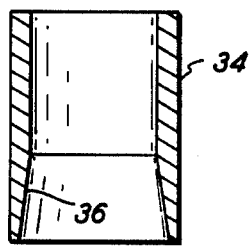
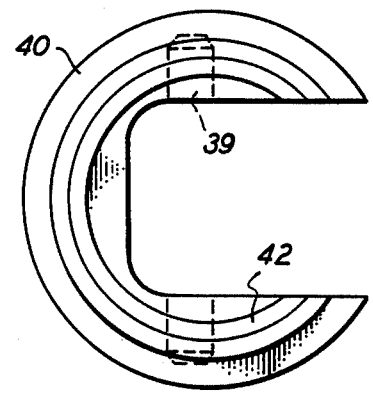
FIG. 4          FIG. 7

BALL TYPE BUR GRIPPING MECHANISM FOR DENTAL HANDPIECE

BACKGROUND AND SUMMARY OF THE INVENTION

The present invention is directed to a bur gripping mechanism for use in a high speed dental handpiece. Various systems are known and are commonly used for releasably holding dental burs in place. They include collet chucks of both the pushout and drawback types, and spring grip chucks.

In the present invention, the traditional chuck is eliminated in favor of a ball-type gripping mechanism providing a positive gripping engagement with the shank of a dental bur. Gripping balls are carried in a ball carrier which surrounds the bur shank. The ball carrier is seated on a spring which urges the ball carrier and its entrained balls into operative engagement with the inner wall of a conical or tapered ramp, which surrounds the ball carrier and which in turn forces the balls inward against the bur shank. The balls indent the softer material of the bur shank for positive engagement. An externally applied force on the ball carrier against the spring releases the balls from engagement with the bur shank.

DRAWING

FIG. 2 is a sectional view of a ball carrier which is one of the components of FIG. 1.

FIG. 3 is an axial section along the line III—III of FIG. 2.

FIG. 4 is a sectional view of a bushing which is one of the components of FIG. 1.

FIG. 7 is a bottom view of the lever housing of FIG. 1.

DESCRIPTION

Figure 1:
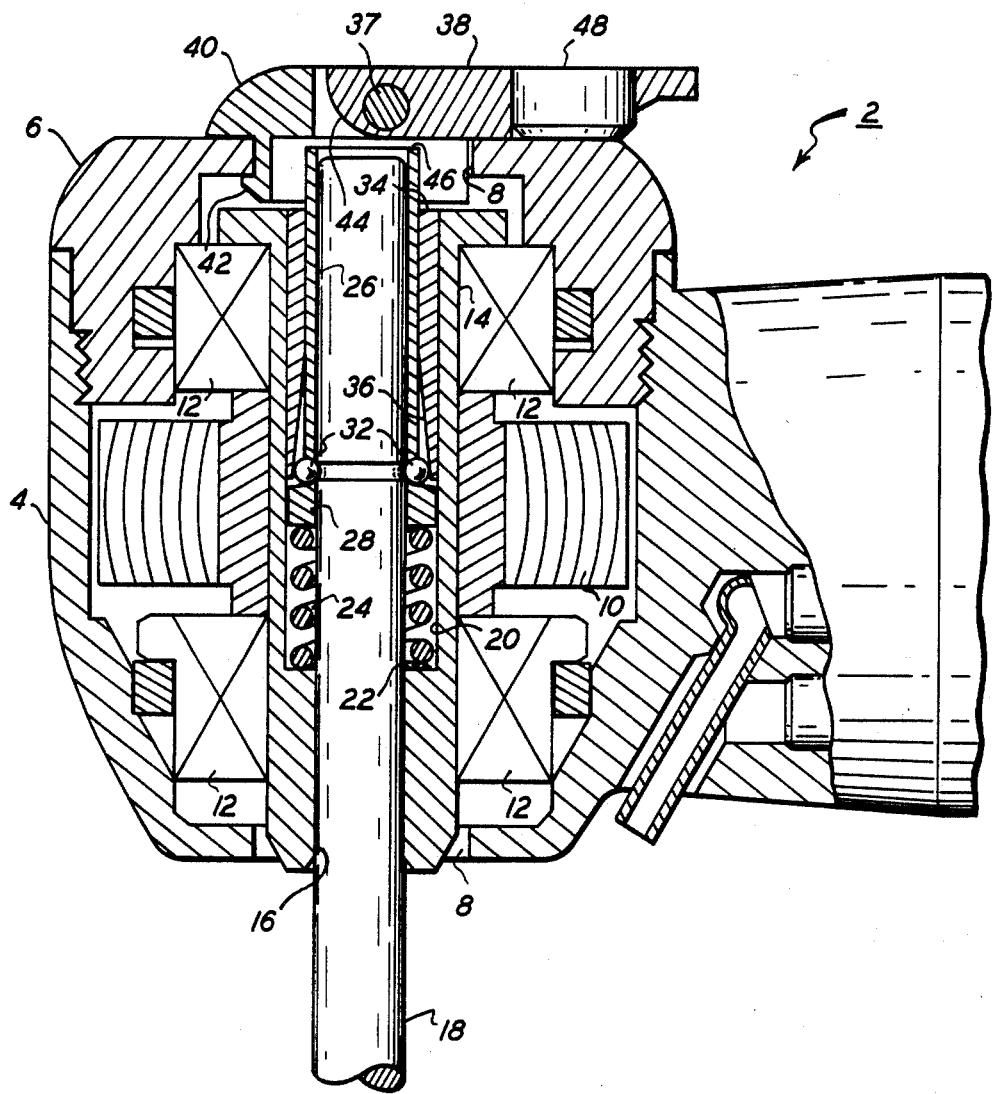
FIG. 1 is a side elevation, partly in section, of the head of a dental handpiece incorporating the present invention.

Referring to FIG. 1, the head portion of a dental handpiece is generally indicated at 2 and includes a housing 4 into which a cap 6 is threaded. Housing 4 and cap 6 together form an internal cavity and top and bottom axial apertures 8. An air turbine 10 is rotatably mounted on bearings 12 which are in turn mounted within the housing and cap, all of which is well known in the art.

A flanged cylindrical bur tube or rotor tube 14 is fixed to the turbine rotor 10 and is rotatably mounted within the bearings 12. Bur tube 14 includes an axial bore 16 therethrough into which the shank of a dental bur 18 is slidable. At the lower portion of bur tube 14, bore 16 is of a pilot diameter into which bur 18 fits freely but closely. The upper portion of bur tube 14 is counterbored to a larger diameter, the counterbore 20 providing an internal circumferential shoulder 22. A helical compression spring 24 is seated on the shoulder 22.

An open cylindrical ball carrier 26, (see also FIGS. 2 and 3) including a lower flange 28, has an internal bore 16' of generally the same inside diameter as the pilot diameter 16 of bur tube 14. Ball carrier 26, by means of its lower flange 28, is seated atop the compression spring 24. Ball carrier 26 includes a number of wall openings 30, disposed around its circumference above the flange 28 for the containment of a ball 32 in each one. Openings 30 are conically configured so that balls 32 can extend through the wall of carrier 26 but cannot pass through it. Accordingly, the balls 32 are trapped in their individual openings 30 by the surrounding bur tube 14.

A bushing member 34 (see also FIG. 4) has an outer cylindrical surface which is press fit into the upper portion of bur tube 14. The inner surface of bushing 34 is conical or tapered (opening downwardly) up to an intermediate point from which the inner surface is cylindrical. The tapered inner surface 36 provides a ramp for the balls 32.

In FIG. 1, in the relative positions of ball carrier 26 and bushing 34 (or ramp 36) that are shown there, the spring 24 is in compression pushing upward on flange 28 of the ball carrier 26. Flange 28 serves also to keep the ball carrier centered within the counterbore 20. The several balls 32 are forced inwardly by the tapered ramp 36 to engage the shank of a dental bur 18. Balls 32 not only engage the bur shank; they make indentations in it creating a positive bite engagement with the shank, securely holding the bur. Balls 32 and bushing 34 (ramp 36) are of harder material than bur shank 18 and therefore are able to make such impressions or indentations in the shank.

From the FIG. 1 position, in which bur 18 is secured, a downward displacement of ball carrier 26 relative to the bushing 34 and ramp 36 (i.e. pushing ball carrier 26 down against spring 24) releases balls 32 from engagement with the bur shank which is thereupon easily removable from the bur tube 14.

One convenient and effective means to move the ball carrier down against the spring 24, for releasing the bur shank or to permit insertion of a bur shank, is shown in FIG. 1. A cam lever 38 is pivotally mounted on a lever housing 40 by means of a pin 37 within holes 39 in housing 40. Lever housing 40 includes a depending resilient flange 42 for snap engagement within the top opening 8 of cap 6. Housing 40 and depending flange 42, as seen in the bottom view of FIG. 7, are C-shaped so as to be resilient for snap engagement within the cap opening 8. Cam lever 38 includes a cam surface 44 which, when lever 38 is raised, bears on the top end face 46 of the ball carrier 26 and moves it downward. The width of the cam lever 38 and its cam surface (that is, its dimension in the direction toward and away from the viewer) is such that the cam surface 44 contacts the end face 46 of the ball carrier when the cam is in use. Lever 38 includes a magnet 48 to hold the lever in a fixed closed position on cap 6 when it is not in use.

The snap fit of the lever housing 40 within the top opening of the cap 6 permits housing 40 to be rotated on the cap in order to orient the cam lever 38 in a position most convenient to the user. The lever housing 40 is not loose or freely rotatable, but rather is snugly fit and rotatable to a desired position where it will remain unless moved intentionally.

Figure 5:
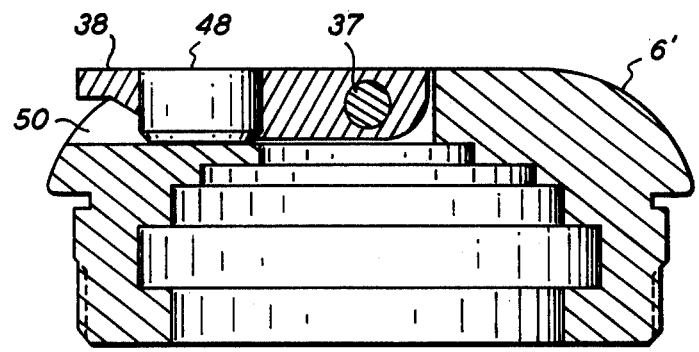
FIG. 5 is a sectional view of a cap in an alternative embodiment of this invention.
Figure 6:
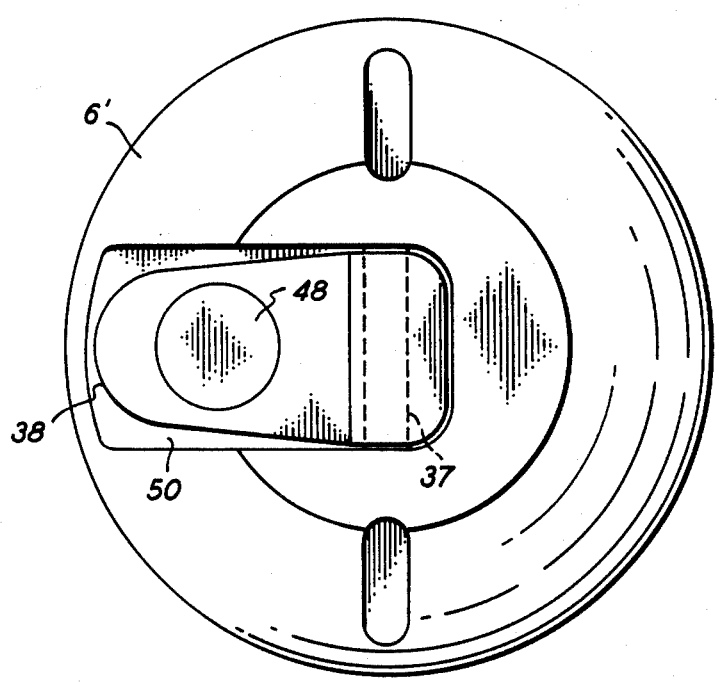
FIG. 6 is a top view of the cap of FIG. 5.

FIGS. 5 and 6 show another configuration of the cap and cam lever of this invention. It will be recalled that in the FIG. 1 arrangement, the cam lever 38 is mounted in its own housing 40 which is in turn rotatably mounted on the cap 6. In the arrangement of FIGS. 5 and 6, cam lever 38 is directly housed in the cap 6' and seats in a recess 50 in the cap. In this arrangement, the cam lever 38 is not rotatable about the axis of the cap as it is in FIG. 1, but the overall height of the head is reduced by the absence of the separate lever housing 40 of FIG. 1. This is a more compact arrangement, though the rotatable cam lever arrangement of FIG. 1 is presently preferred.

In order to prevent contact between the high-speed rotating ball carrier 26 and the stationary cam lever 38, a small clearance is provided between the end face 46 of the ball carrier and the cam lever when the cam lever is in its down position.

An advantage of using a cam lever, in addition to the mechanical advantage it affords, is that it can be left in its rasied position (at which the bur gripping mechanism is open) where it will remain, without being held, while the user removes a bur, selects another one, and so on. Accordingly, a cam lever is my preferred means for actuating this mechanism. However, it is possible to use a straightforward push button on the top of the cap by which thumb-applied force is transmitted to the ball carrier to push it down. A push button may also be desirable for reasons of economy.

The preferred gripping elements in this device are the balls 32. However, it is contemplated that other gripping elements might be used. Cylindrical elements are one example.

What is claimed is:

1. A head for a dental handpiece, including:
   a rotor tube disposed for rotation within said head, said rotor tube having an inner ramp surface in its upper portion and an inner circumferential shoulder at a lower portion,
   a spring disposed within said rotor tube on said shoulder,
   a grip carrier disposed within said rotor tube on said spring, said grip carrier entraining in its wall a gripping element for operative engagement and disengagement with said ramp surface,
   said rotor tube and said grip carrier surrounding an axial bore for the reception of a bur shank, and
   a cam lever pivotally mounted to said head in operative relationship with said grip carrier, said cam lever being movable to an open position to move said grip carrier against said spring and to a closed position to return said grip carrier under the influence of said spring into operative engagement with said ramp surface whereby said gripping element is urged into engagement with a bur shank in said bore.

2. A device as defined in claim 1 in which said gripping element is a ball.

3. A device as defined in claim 1 including a plurality of said gripping elements disposed around said grip carrier.

4. A device as defined in claim 3 in which said gripping elements are balls.

5. A device as defined in claim 1 in which said cam lever is rotatably movable about the axis of said head to an orientation relative to said handpiece to suit the convenience of the user.

6. A device as defined in claim 1 in which said cam lever is recessed within said head so as to be generally flush with the top thereof.

7. A device as defined in claim 1 in which said gripping element is urged into positive engagement with said bur shank by forming indentations therein.

8. A device as defined in claim 1 further including safety means to hold said cam lever in its closed position.

9. A device as defined in claim 8 in which said safety means is a magnet mounted in said cam lever for engagement with said head.

* * * * *